(12) United States Patent
Deem et al.

(10) Patent No.: US 9,447,781 B2
(45) Date of Patent: Sep. 20, 2016

(54) OSMOTICALLY DRIVEN DISPENSE PUMP AND RELATED COMPONENTS FOR USE IN HIGH PRESSURE APPLICATIONS

(75) Inventors: Trent Deem, Bountiful, UT (US); Phil Ligrani, Osford (GB); Bradley C. Hansen, La Jolla, CA (US)

(73) Assignee: University of Utah Research Foundation, Salt Lake City, UT (US)

( * ) Notice: Subject to any disclaimer, the term of this patent is extended or adjusted under 35 U.S.C. 154(b) by 1729 days.

(21) Appl. No.: 11/996,450

(22) PCT Filed: Jul. 21, 2006

(86) PCT No.: PCT/US2006/028141
§ 371 (c)(1),
(2), (4) Date: Jun. 5, 2008

(87) PCT Pub. No.: WO2007/013957
PCT Pub. Date: Feb. 1, 2007

(65) Prior Publication Data
US 2008/0269725 A1 Oct. 30, 2008

Related U.S. Application Data

(60) Provisional application No. 60/702,028, filed on Jul. 22, 2005.

(51) Int. Cl.
| | | |
|---|---|---|
| *A61K 9/00* | (2006.01) | |
| *A61M 5/145* | (2006.01) | |
| *F04B 17/00* | (2006.01) | |

(52) U.S. Cl.
CPC ............. *F04B 17/00* (2013.01); *A61K 9/0004* (2013.01); *A61M 5/145* (2013.01); *A61M 2005/14513* (2013.01)

(58) Field of Classification Search
CPC .............. A61K 9/004; A61K 9/0024; A61M 2005/14513; A61M 5/145; A61M 5/14248; A61M 5/1409; A61M 2205/75; A61M 2209/045; B01J 4/04
USPC ............. 604/82–85, 92, 134, 135, 230, 231, 604/416, 518, 519, 892.1, 140, 141, 143, 604/144, 145
See application file for complete search history.

(56) References Cited

U.S. PATENT DOCUMENTS

| | | | |
|---|---|---|---|
| 3,214,067 A | | 10/1965 | Linington |
| 3,219,573 A | * | 11/1965 | Chen et al. .................... 204/636 |

(Continued)

OTHER PUBLICATIONS

Yu-Chuan Su, et al.; A Water-Powered Osmotic Microactuator; Journal of Microelectromechanical Systems, vol. 11, No. 6; Dec. 2002; pp. 736-742.

(Continued)

*Primary Examiner* — Emily Schmidt
*Assistant Examiner* — Lauren M Peng
(74) *Attorney, Agent, or Firm* — Thorpe North & Western, LLP

(57) ABSTRACT

A high pressure osmotic dispense pump (10) having a substantially continuous delivery rate and extended delivery times is described and disclosed. The dispense pump (10) includes a semi-permeable membrane (12) which is substantially free of distortions and lateral stretching stresses. The membrane housing (14) and configuration of the present invention allows for consistent and accurate flow rates at the micro-liter level and improved control of the surface area of the semi-permeable membrane (12). This osmotic pump (10) also includes optional methods for activating and deactivating the osmotic process and/or controlling flow rates. Along with these features, the pump can be amplified or modulated to increase the dispense rate and/or adjust the flow rate during operation.

22 Claims, 8 Drawing Sheets

(56) References Cited

U.S. PATENT DOCUMENTS

| | | | |
|---|---|---|---|
| 3,604,417 A * | 9/1971 | Stolzenberg | A61M 3/00 222/389 |
| 3,760,804 A | 9/1973 | Higuchi et al. | |
| 3,987,790 A | 10/1976 | Eckenhoff et al. | |
| 3,995,631 A | 12/1976 | Higuchi et al. | |
| 3,995,632 A | 12/1976 | Nakano et al. | |
| 4,034,756 A | 7/1977 | Higuchi et al. | |
| 4,203,439 A | 5/1980 | Theeuwes | |
| 4,327,725 A | 5/1982 | Cortese et al. | |
| 4,331,728 A | 5/1982 | Theeuewes | |
| 4,340,048 A | 7/1982 | Eckenhoff | |
| 4,474,575 A | 10/1984 | Eckenhoff et al. | |
| 4,539,004 A | 9/1985 | Eckenhoff et al. | |
| 4,633,765 A * | 1/1987 | Knodel | 92/248 |
| 4,765,989 A | 8/1988 | Wong et al. | |
| 4,838,862 A | 6/1989 | Baker et al. | |
| 5,147,328 A * | 9/1992 | Dragosits et al. | 604/218 |
| 5,279,608 A * | 1/1994 | Cherif Cheikh | A61M 5/145 604/131 |
| 5,876,377 A | 3/1999 | Kriesel | |
| 5,935,593 A | 8/1999 | Ron et al. | |
| 6,095,491 A * | 8/2000 | Kriesel | 251/206 |
| 6,436,091 B1 | 8/2002 | Harper et al. | |
| 6,632,217 B2 | 10/2003 | Harper et al. | |
| 6,641,561 B1 * | 11/2003 | Hill | A61M 5/2066 604/136 |
| 6,740,077 B1 * | 5/2004 | Brandau | A61K 9/0004 604/892.1 |
| 6,840,931 B2 | 1/2005 | Peterson et al. | |
| 2005/0010175 A1 | 1/2005 | Beedon et al. | |
| 2005/0070884 A1 | 3/2005 | Dionne et al. | |
| 2005/0101943 A1 | 5/2005 | Ayer et al. | |

OTHER PUBLICATIONS

Kaushal, et al.; An Update on Osmotic Drug Delivery Patents; Pharmaceutical Technology, Aug. 2003; pp. 38-44; 97.

Williams, et al.; Osmotically-Driven Micro-Dispense Pump; Utah State Center of Excellence for Biomedical Microfluidics; www.mems.utah.edu/Project_Pages/Micropumps/Osmotic_Pumps.htm; accessed from website Jun. 28, 2005; pp. 1-4.

Hia Bang Lee, et al.; Evolution of the Patent for Osmotic Drug Delivery; J. Kor. Pharm. Sci., vol. 32, No. 4, 2002; pp. 241-258.

* cited by examiner

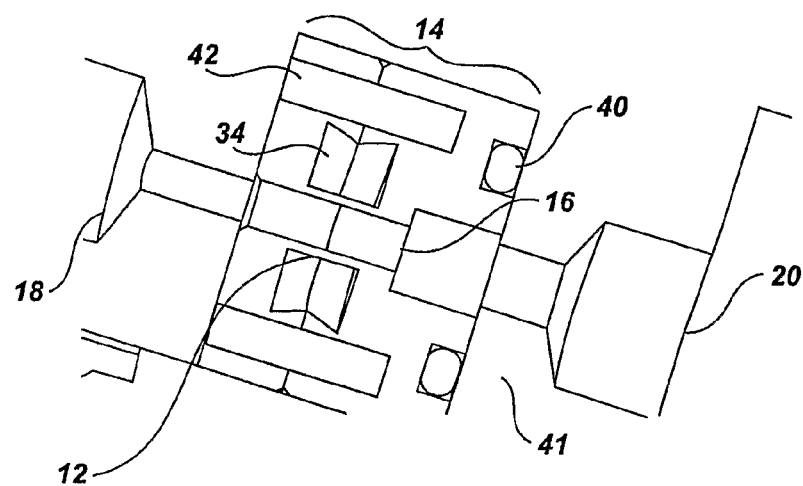
Fig. 2b
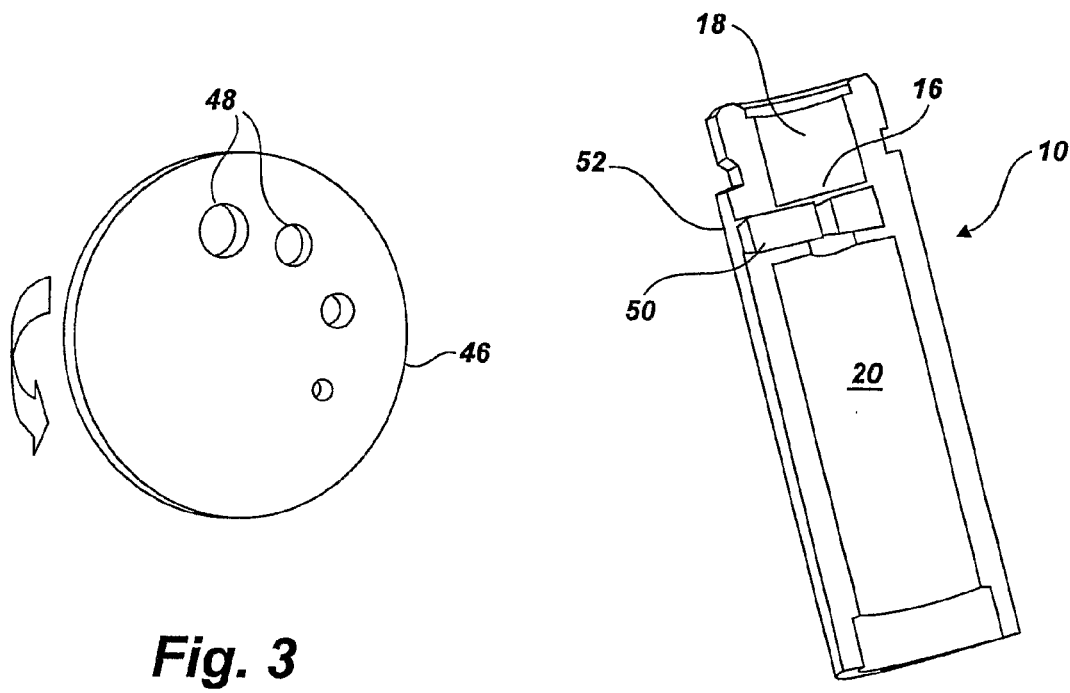
Fig. 3
Fig. 4a

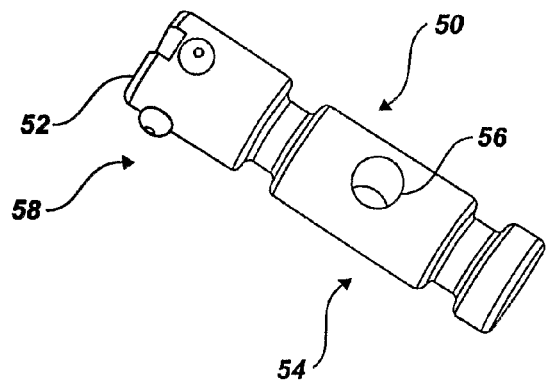
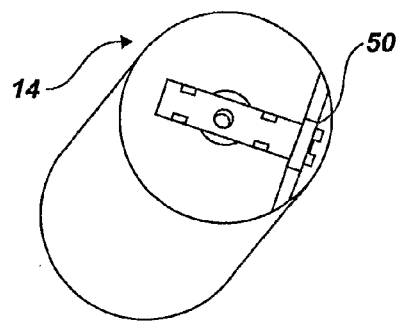
Fig. 4b          Fig. 4c
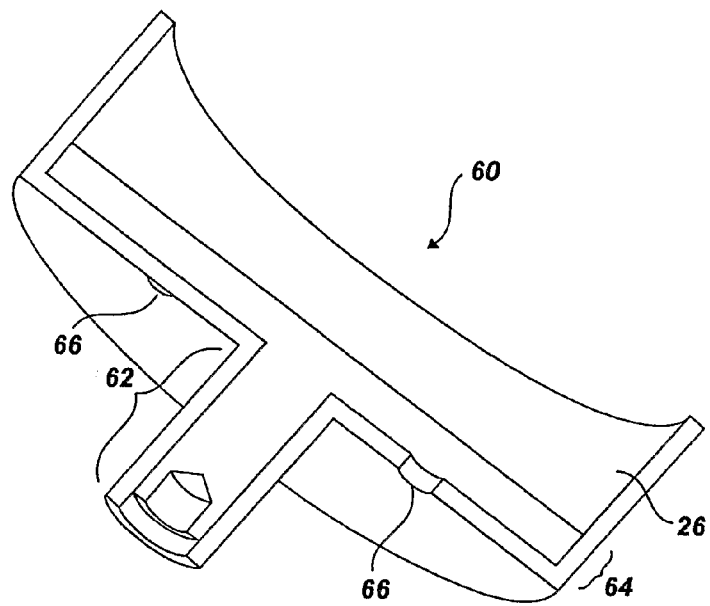
Fig. 5

US 9,447,781 B2

OSMOTICALLY DRIVEN DISPENSE PUMP AND RELATED COMPONENTS FOR USE IN HIGH PRESSURE APPLICATIONS

RELATED APPLICATIONS

This application claims the benefit of earlier filed U.S. Provisional Patent Application No. 60/702,028, filed Jul. 22, 2005, which is incorporated by reference herein in its entirety.

FIELD OF THE INVENTION

The present invention relates to osmotically driven pumps. Accordingly, the present invention involves the fields of chemistry, physics, micromechanical devices, engineering, and materials science.

BACKGROUND OF THE INVENTION

Devices suitable for delivering very small volumes of fluid have been available for several decades. Osmotic pumps are of particular interest for delivering small amounts of drugs or other similar applications. These osmotic pumps typically utilize a driving force based on a concentration gradient across a semi-permeable membrane. Most current designs involve a variety of flexible housings and may include one or more chambers. Unfortunately, these pumps tend to have limited control over the flow rate. Specifically, the flexible housings and membranes can create fluctuations in flow rate which are unpredictable. Although this may be acceptable in some applications, fluctuations in flow rate can generally be unacceptable for applications requiring more precise flow rates. In addition, any changes in contours or surface area of the semi-permeable membrane can affect the flow rate of solvent across the membrane.

Furthermore, continuous precise delivery of fluids for extended periods of time can present a unique challenge to these types of devices. Most often, current technologies are limited to delivery times of several weeks to a couple of months. If used in a patient, this requires frequent replacement and can be inconvenient. Further, such short useful durations increase costs associated with replacement, maintenance, and materials.

As such, cost effective systems and devices that are capable of effectively delivering relatively small volumes of fluids over an extended period of time continue to be sought through ongoing research and development efforts.

SUMMARY OF THE INVENTION

Accordingly, the present invention provides a high pressure osmotic dispense pump having a substantially continuous delivery rate and extended delivery times. The dispense pump can include a semi-permeable membrane which is substantially free of distortions and lateral stretching stresses. Generally, the dispense pump of the present invention operates using an osmotic process driven by a concentration gradient of solvent across a selectively permeable membrane. A solvent reservoir and a solution reservoir can be fluidly connected on either side of the semi-permeable membrane. The reservoir chambers can be formed to include pistons which can move to accommodate changes in volumes as the solvent diffuses across the membrane. The membrane housing and configuration of the present invention allows for consistent and accurate flow rates at the micro-liter level and improved control of the surface area of the semi-permeable membrane.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

BRIEF DESCRIPTION OF THE DRAWINGS

FIG. 2b is a cutaway view of a membrane housing including an O-ring seal for high pressure applications in accordance with another embodiment of the present invention.

FIG. 3 is a flow rate modulator having multiple orifice sizes in accordance with another embodiment of the present invention.

FIG. 4a is a cutaway view of a flow control valve housed in a dispense pump along the flow channel in accordance with one embodiment of the present invention.

FIG. 4b is a perspective view of a flow control valve showing detents, flow channel opening and screw slot in accordance with one embodiment of the present invention.

FIG. 4c is a top cutaway view of a flow control valve housed in a dispense pump along a flow channel and in open position in accordance with one embodiment of the present invention.

FIG. 5 is a cutaway view of an osmotic amplifier in accordance with another embodiment of the present invention.

Figure 1:
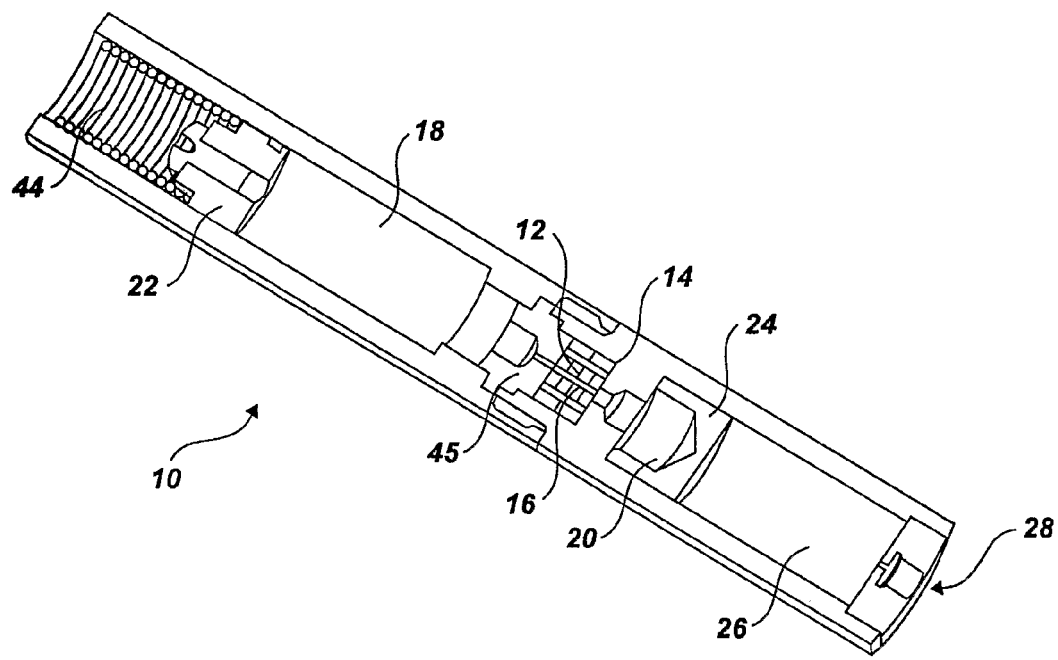
FIG. 1 is a cutaway view of an osmotic dispense pump in accordance with an embodiment of the present invention.

It will be understood that the above figures are merely for illustrative purposes in furthering an understanding of the invention. Further, the figures are not necessarily drawn to scale, thus dimensions and other aspects may vary to make illustrations thereof clearer. Therefore, departure can be made from the specific dimensions and aspects shown in the figures in order to produce the devices of the present invention.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a reservoir" includes one or more of such spaces, reference to "a gasket" includes reference to one or more of such materials, and reference to "charging" includes reference to one or more of such steps.

DEFINITIONS

In describing and claiming the present invention, the following terminology will be used in accordance with the definitions set forth below.

As used herein, "securing forces" are those forces which contact or otherwise influence the position, motion, or stresses of the semi-permeable membrane relative to materials which directly contact the membrane.

As used herein, "direct contact" refers to a spatial relationship of two materials where each of the identified materials is in physical contact with the other.

As used herein, "lateral clamping" refers to securing the semi-permeable membrane using substantially only lateral forces with respect to the plane of the membrane surface.

As used herein, "distortions" refers to non-planar bends, curves or other features which substantially change the exposed surface area of the membrane compared to a perfectly planar configuration. Thus, a membrane which is substantially free of distortions allows for some minor variation from planar which does not cause flow rate fluctuations greater than about 10%.

As used herein, "fluid communication" refers to any passage, channel, system of channels, or volume where fluid can pass between the identified reservoirs.

As used herein, "substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent. Particularly, elements that are identified as being "substantially free of" are either completely absent, or are included only in amounts which are small enough so as to have no measurable effect.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, dimensions, volumes, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 1 micrometer to about 5 micrometers" should be interpreted to include not only the explicitly recited values of about 1 micrometer to about 5 micrometers, but also include individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

Invention

In accordance with the present invention, a high pressure osmotic dispense pump can be formed as shown in FIG. 1. The dispense pump 10 can include a semi-permeable membrane 12. This semi-permeable membrane can be substantially free of distortions and lateral stretching stresses. By having a semi-permeable membrane substantially free of distortions and lateral stretching stresses, a more continuous flow across the membrane may be maintained and/or controlled. This increased control of flow over the membrane is particularly desirable in situations dealing with small amounts of transfer of fluid across the membrane, e.g. less than about 2 to 3 micro-liters per hour. In situations such as these, even minor inconsistencies in allowing quantities of fluid to cross the membrane can have an undesirable effect on the overall application and use of the device. Additionally, by assembling and maintaining a membrane that is substantially free of distortions and lateral stretching stresses, the overall integrity of the membrane can be preserved. Without distortions and lateral stretching stresses, the membrane itself is not subject to unwanted stresses that can decrease the working life of the membrane. Perhaps more importantly, without such unwanted stresses, the membrane can function in a consistent manner across the exposed surface. On a very small scale, an added benefit of a membrane installed that is substantially free of distortions and lateral stretching stresses is that it allows for more precision and compaction in the overall device assembly. As such, the semi-permeable membrane can be secured within a membrane housing 14 across a flow channel 16.

The dispense pump of the present invention operates using an osmotic process driven by a concentration gradient of solvent across the selectively permeable membrane. The flow rate from osmosis is partially a function of the exposed surface area of the semi-permeable membrane 12 to a solvent and solution reservoir on either side of the membrane which can be connected by the flow channel 16. The solvent reservoir 18 can contain a first fluid such as a solvent, e.g. pure water, and the solution reservoir 20 can contain a solution of the solvent and a solute, e.g., concentrated NaCl. The solution of solvent and solute is generally initially charged to a specific concentration. The concentration can be determined by the overall design of the pump, and other considerations such as the anticipated quantity and duration of dispensing a dispensing fluid. In order to attain consistent and accurate flow rates at the micro-liter level, the surface area of the semi-permeable membrane can be carefully controlled as discussed in more detail below.

Further, the solvent reservoir 18 can be in fluid communication with the semi-permeable membrane 12. A solvent piston 22 can be configured to be movable in response to changes in a volume of fluid in the solvent reservoir. For example, the solvent piston can be oriented in a cylindrical solvent reservoir opposite the semi-permeable membrane. Similarly, the solution reservoir 20 can be in fluid communication with the semi-permeable membrane and can include a delivery piston 24 which is movable in response to changes in volume of a fluid in the solution reservoir. A dispense fluid reservoir 26 can also be adjacent the delivery piston opposite the solution reservoir which is fluidly isolated from each of the solvent reservoir and solution reservoir. The fluid reservoir can also include an outlet 28 for delivering a fluid contained in the fluid reservoir as the delivery piston moves in response to an increase in the volume of the solution reservoir as fluid moves across the semi-permeable membrane. Ideally, as fluid from the solvent reservoir 18 crosses the membrane and flows into the solution reservoir through osmosis, the delivery piston works on the dispense fluid reservoir so as to cause a dispensing fluid, such as a pharmaceutical aid, to dispense out of the pump through the outlet. The outlet can be any suitable opening which allows fluid to exit the dispense fluid reservoir without also allowing external fluids to enter the pump. The outlet can be a one-way valve or an open aperture where the dispense fluid has a viscosity to prevent inward flow of external fluid. Further, the outlet can also be connected to a catheter or to another similar type of system for injection into human or animal subjects. Alternatively, the outlet may be connected to or may lead to a fluid mechanic passage flow device.

The reservoirs, pistons and various portions of the dispense pumps of the present invention can be formed of any suitable material. Suitable materials can preferably be mechanically strong, chemically resistant to corrosion, and do not adversely react with charge solutions, e.g., solvent, solute, dispense fluid, etc., or the surrounding environment. Most often the pump parts can be formed of biologically compatible materials. Accordingly, the solvent piston 22 and the delivery piston 24 can be formed of a material such as, but not limited to, polyether ether ketone (PEEK), polyimides such as VESPEL, KAPTON, acrylic, metal, polycarbonate, glass reinforced TEFLON, and composites or combinations thereof. Currently, polymer materials are preferred to form the pistons. Typically, each of the solvent reservoir 18, solution reservoir 20, and dispense fluid reservoir 26 can have rigid walls. In this way, the dispense pumps of the present invention can be used repeatedly with consistent and reliable performance.

In an additional aspect of the present invention, interior surfaces of at least one of the solvent reservoir 18, solution reservoir 20, and dispense fluid reservoir 26 can include a coating of polytetrafluoroethylene or other material having a low coefficient of friction. Many materials can result in binding of the pistons along the interior walls of the reservoirs. This undesirable situation can result in discontinuous flow or complete blockage. Internal coatings can further prevent or reduce discontinuous flow and blockage. Other coating materials such as, but not limited to, thermoplastics, durable paints, and sealants can also be used for this purpose.

Alternatively, in some cases, the interior surfaces of at least one of the solvent reservoir 18, solution reservoir 20, and dispense fluid reservoir 26 can include a coating of a material having a relatively high coefficient of friction. Purposefully slowing the movement of the pistons along the interior walls of the reservoirs is another design consideration which can produce a consistent and relatively slow pump action. A design characteristic of this type would be most useful in systems where there is a desire to greatly slow the osmosis process and results, thereby reducing the overall amount of dispense fluid dispensed from the outlet 28 per unit of time. Furthermore, a material having a relatively high coefficient of friction need not be used. Rather, any coating material having a known coefficient of friction, or known action of the system may be used. Once the result on the system is known, the parameters of the system may be designed so as to properly account for the retarded piston movement.

One important aspect of the present invention is the membrane housing 14 and corresponding positioning of the semi-permeable membrane 12. As stated previously, the surface area of the semi-permeable membrane is one controlling feature for flow rate since the osmotic process is a strong function of this parameter. Also stated earlier is the importance of a membrane which is substantially planar and free of distortions and lateral stretching stresses as the distortions and unwanted stresses can cause, among other things, inconsistencies in the flow rate. Of course, other variables can also influence flow rate such as membrane material, membrane thickness, temperature, solvent-solute system, spring strength, and the like. However, the surface area of the membrane has a large affect on the variations in flow rate during use. Further, the semi-permeable membrane can have an exposed surface area which is smaller than a covered surface area. By covering more of the surface of the membrane than exposing, additional securing strength can be provided by the membrane housing.

The present invention can have improved flow rate control characteristics over conventional designs at least partially because of the membrane housing configuration. The membrane housing 14 can yield improved and tighter control of exposed surface area of the membrane 12 resulting in highly controlled flow rates. Specifically, when the membrane is loose or otherwise has a non-planar profile, the flow rate can tend to be non-continuous as the surface area can change as the membrane moves, or as leaks develop around the membrane. The configurations provided by the present invention can allow for fluid delivery at a flow rate which is substantially continuous. For example, the delivery flow rate can be tuned to within about 50 pL/hr and is non-pulsed, and preferably within about 20 pL/hr. Generally, the delivery flow rate can have a variation of less than about 10%, preferably less than about 5%, and most preferably less than about 2%.

Figure 2A:
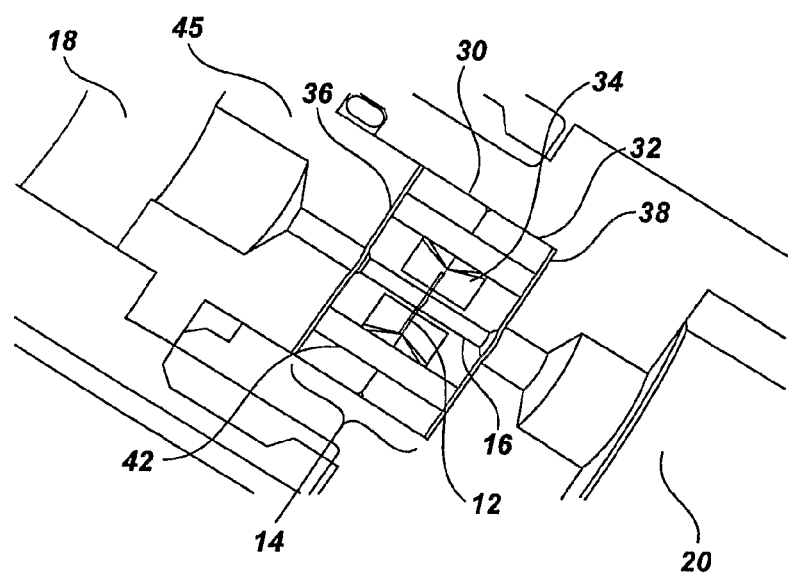
FIG. 2a is a cutaway view of a membrane housing including a gasket in accordance with another embodiment of the present invention.

Although a number of configurations can be used in the membrane housings 14 of the present invention, the semi-permeable membrane 12 can be secured by lateral clamping between two members. For example, FIG. 2a illustrates an enlarged cutaway view of the membrane housing 14 and immediately surrounding portions of the dispense pump in accordance with one embodiment of the present invention. A semi-permeable membrane 12 can be secured between two flow channel members 30 and 32. In this embodiment, a polydimethylsiloxane (PDMS) or room temperature vulcanization (RTV) gasket 34 is used to retain the edges of the semi-permeable membrane. Further, gaskets 36 and 38, preferably of the TEFLON type can be used at the interface between the flow channel members and each of the solvent reservoir 18 and solution reservoir 20, respectively. FIG. 2b illustrates a cutaway view of a membrane housing 14 having an O-ring seal 40 for higher pressure applications than is generally achievable using a TEFLON gasket. The O-ring prevents leakage along the plane between the membrane housing and the delivery chamber body 41. Therefore, the actual seals and gaskets used should be determined based on the particular application.

As part of the membrane housing 14, a flow channel 16 can be formed in at least two membrane housing members to form a fluid connection between the solvent reservoir 18 and the solution reservoir 20. The flow channel in each membrane housing member can be substantially aligned such that interfaces along the flow channel have substantially no incongruities. In each embodiment illustrated in FIGS. 2a and 2b, the housing flow channel on both sides of the membrane 12, as well as alignment stud holes 42 can be fabricated during the same operation to attain exact alignment. This technique has been used and verified on several prototypes showing improved repeatability as well as predictability in performance for flow rates ranging from 0.3 to 1 micro-liter per hour. The fabrication of alignment holes and flow channels can be done by laser cutting, EDM electro-discharge machining, or other precision machining techniques.

In this manner, the membrane can be secured using substantially only lateral clamping which avoids distortions or stretching of the semi-permeable membrane 12 that occur when using threaded securing of the membrane. Thus, for example, the membrane housings shown in FIGS. 2a and 2b can be assembled by laying one half of the PDMS or RTV gasket 34 in one of the two flow channel members 30 or 32 and then laying the semi-permeable membrane 12 on the PDMS gasket. Alignment studs such as rods, screws, or other suitable members can be placed in the alignment holes 42 of one of the two flow channel members. The second half of the PDMS gasket and channel member can then be brought toward the first half along a lateral path which is substantially perpendicular to the plane of the semi-permeable membrane and the alignment studs secured in place.

However, any method of securing the semi-permeable membrane 12 between the at least two membrane housing members using substantially only securing forces which are perpendicular to the semi-permeable membrane can also be used. For example, the membrane can be secured by orienting the semi-permeable membrane between two membrane housing members and inserting at least two alignment members into corresponding alignment channels as illustrated in FIGS. 2a and 2b. These alignment channels can be substantially perpendicular to the semi-permeable membrane such that the two membrane housing members are pressed towards one another with substantially only forces acting perpendicular to the semi-permeable membrane.

The membrane 12 can be completely enclosed within the PDMS or RTV gasket 34 with the only exception being the area open and exposed to the flow channel 16. This enclosure ensures that the flow is restricted to the desired flow channel and can travel through no other path. This membrane housing 14 is not the only method to achieve proper control of the flow area. Other simplified methods of flow control have been formulated which are optimal for bulk manufacturing of the product. For example, the membrane housing components can be molded of a rigid rubber or suitable plastic that will properly align the flow channels when the membrane is pressed between these members. Further, part of or all of the membrane housing can be formed as part of the pump housing. Generally, the TEFLON gasket 38 and PDMS or RTV gasket arrangement shown in FIG. 2a is operational for pressures up to 70 psig. Additionally, the O-ring seal 40 and PDMS/RTV gasket arrangement shown in FIG. 2b can be operational for pressures up to 250 psig or higher with suitable pump housing rigidity.

The semi-permeable membrane 12 can be formed of any suitable material which selectively allows specific species to permeate while restricting passage of other species. Typically, this selectivity can be between a solvent and a solute although other types of membranes can also be useful. Most often the selectivity can be based on the respective sizes of the species, however, any known selectivity can be used. A number of semi-permeable membrane materials which can be used include, but are in no way limited to, polyimide, polyamide, porous glass, cellulose acetate, composites thereof, or the like. An added benefit of the present invention is that a circular or nearly-circular shaped membrane is not required. Rather, nearly any shape would work with the present configuration. Because a significant portion of the membrane is covered compared to the exposed portion, the membrane need not have exact dimensions during assembly for effective performance. Additionally, the means of securing allows for greater variation and less precision in the shape of the membrane.

Referring again to FIG. 1, an optional spring 44 can be used to pressurize the solvent reservoir 18. The spring can be operatively oriented adjacent the solvent piston 22 opposite the solvent reservoir 18 to displace the solvent piston towards the semi-permeable membrane 12 as solvent diffuses across the membrane into the solution reservoir 20. This spring can keep the solvent in contact with the membrane regardless of orientation, and thus facilitate osmosis. Further, the spring can pressurize the solvent reservoir to elevate the boiling temperature of the solvent to achieve higher operating temperatures. Higher operating temperatures can be desired to increase flow across the membrane and increase consistency in flow rate. Also, the spring can help to ensure that the solvent piston remains in contact with the solvent reservoir. In yet another optional embodiment, the spring can be selected or designed to have a desired strength in order to increase or decrease delivery flow rates. Differences in pressure across the membrane can contribute to a chemical potential gradient and thus osmotic flow rates.

Additionally, an optional membrane housing retainer 45 can be placed adjacent the membrane housing 14 to hold the membrane housing in place during assembly of the pump. The semi-permeable membrane 12 separates the solvent reservoir 18 from the solution reservoir 20. The semi-permeable membrane also allows passage to solvent and restriction to the osmotic agent or solute such as NaCl. The membrane can be formed of a porous material with feature and pore sizes on the order of angstroms in diameter. Any number of solvent-solute systems can be used. Water is the most common solvent, and salt compounds are the most common solutes. Non-limiting examples of suitable systems include water-concentrated aqueous NaCl, KCl, MgCl, other salt compounds, and the like. In addition, the solvent reservoir can be pure solvent or a dilute solution of the solute, depending on the desired delivery flow rates. Furthermore, the solute may be of a coated-type, whereby the concentration is not affected by the coated solute until at least a portion of the coating is dissolved or otherwise removed from the solute. This type of design feature gives further control over the design parameters of the pump in allowing for means to increase the concentration of the solute in the solution reservoir through use of coated solute over time. By boosting the concentration of the solute over time, the osmosis process can be prolonged, thus furthering the dispensing of dispense fluid. Additionally, a combination of solutes, including coated solutes, may be used. Similarly, the solvent reservoir can contain a supersaturated and/or concentration of solute which exceeds solubility. Therefore, as the solute leaves the reservoir additional solute dissolves into solution to maintain a high concentration in the solution reservoir.

The concentration and type of solute in the solution reservoir 20 can affect the flow rate. For example, in some cases, the desired delivery flow rate may be a continuous flow rate over a year, while in other cases the same size pump can be used for delivery of the same amount of fluid over six months by decreasing the concentration of solute in the solution reservoir. The solution reservoir can contain a super-saturated solution of solute sufficient to drive the osmotic process for approximately one year or more.

As pressure builds in the solution reservoir 20 due to diffusion of solvent across the semi-permeable membrane 12 into the solution reservoir, the delivery piston 24 moves forward to increase the volume of the solution reservoir and exerts a pressure on the dispense fluid in the dispense fluid reservoir 26. The delivery fluid can be driven from the dispense reservoir out through the outlet 28 as the osmotic pressure increases.

An optional flow rate modulator can also be used to allow selection of a desired flow rate, making the pump reusable, and more versatile. As shown in FIG. 3, this flow rate modulator can be a circular plate 46 with various sized orifices 48 corresponding to a plurality of flow rates, which can be rotated to the desired flow rate. A modulator plate can be oriented between the semi-permeable membrane 12 and the solvent reservoir 18. Alternatively, the osmotic membrane can be mounted between two modulator plates. In practice, only one orifice is generally exposed to the solvent and osmotic agent reservoir at a time. Rotating the modulator will expose a different sized orifice to increase or decrease the rate. Rotation of the flow rate modulator can be performed manually during use via an external control on the pump housing or during replacement of the semi-permeable membrane and/or during recharging of the reservoirs. In one alternative embodiment, the osmotic membrane can be fixed in place and the flow rate modulator can be located immediately adjacent to the solvent reservoir 18 so that adjustment of the modulator position can be implemented without alteration of or disturbance to the osmotic membrane or its mounting assembly.

Alternatively, the disk 46 can also be rotated to a position with no exposed orifice 48, thereby stopping the osmotic process. Various sliding devices can also be used to perform the same function. A simple sliding valve can be placed next to the membrane on the solution reservoir side that can slide to discontinue contact of the membrane with the solution resulting in cessation of the osmotic process.

In yet another optional embodiment of the present invention, a small flow activation valve can be used to activate and deactivate the osmotic process. Referring now to FIG. 4a, a flow activation valve 50 is shown inserted along the flow channel 16 adjacent to or near the membrane on the side of the solution reservoir 20 of the dispense pump 10. The valve can be rotated 90 degrees using a flat head screw driver or other tool or mechanism to open or close the valve using a screw slot 52. Other configurations may be used to allow for rotation of the valve. A handle that can be manipulated by fingers or pliers or other tools can be equally useful.

FIG. 4b illustrates one embodiment of the flow activation valve 50. The flow activation valve can include a cylindrical member 54 having an open bore 56 laterally therein such that a central axis of the open bore is substantially perpendicular to a central axis of the cylindrical member. When the screw slot 52 is parallel with the housing, the flow channel is open to allow the osmotic process to operate. The process is deactivated when the screw slot is perpendicular to the housing. In one embodiment, the valve can be located directly behind the semi-permeable membrane. Alternatively, the flow activation valve can be oriented between the semi-permeable membrane and the solvent reservoir. Further, the valve can be held in the open and closed positions by alignment detents 58. These detents are simple bumps on the valve that fit into small corresponding holes in the housing that properly align the valve in the on and off positions. FIG. 4c illustrates a top side cutaway view of a detent holding the valve in an open position within the membrane housing.

Alternatively, the dispense pump 10 may have detents and the flow activation valve 50 may have reverse-detents or indents. This configuration operates similar to that presented in FIGS. 4b and 4c, except that the activation valve receives the detents from the dispense pump, rather than the other way around.

The valve 50 can be formed of any suitable material, depending on the application. Non-limiting examples of suitable valve materials can include quality plastics such as polyetheretherketones (PEEK), polyimides such as VESPEL and KAPTON, or the like.

Depending on the use of the pump and desired delivery rate, the flow rate may need to be increased above that delivered by unassisted configurations such as that shown in FIG. 1. One effective way to increase the flow rate is by using a delivery amplifier 60, as shown in FIG. 5, which can increase the flow rate up to about 1,000 times compared to pumps without an osmotic amplifier. The advantage of the amplifier is that a much smaller volume of solvent and solute are used in the osmotic process, compared to a device which dispenses the same amount of delivery fluid without an osmotic amplifier. Thus, the space used by solvent and solute reservoirs can be decreased. The required flow rate can be achieved by appropriately sizing the cross sectional area of the membrane, the solution reservoir, and the delivery reservoir.

Figure 6:
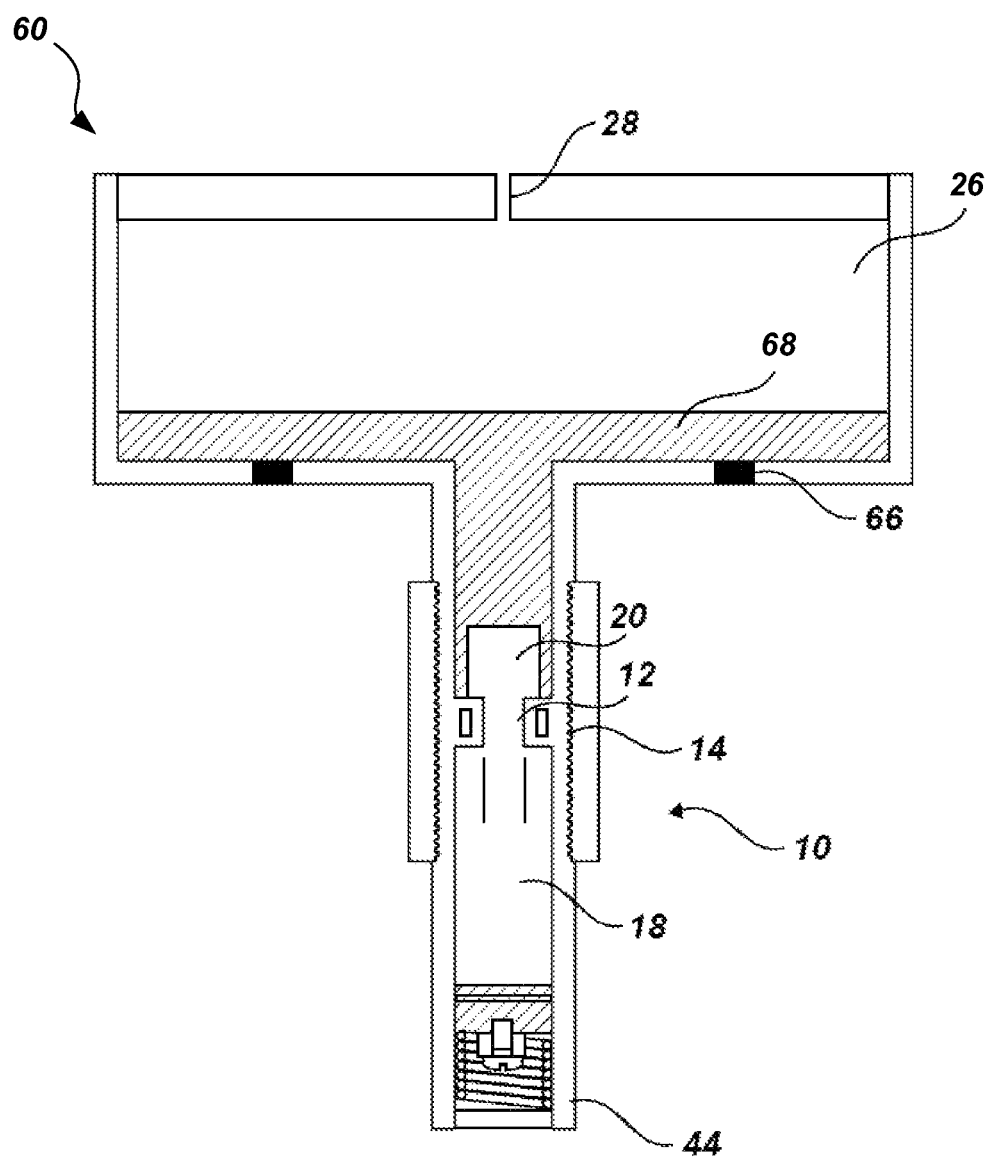
FIG. 6 is a cross-sectional view of an osmotic dispense pump having an osmotic amplifier in accordance with an embodiment of the present invention.
Figure 7:
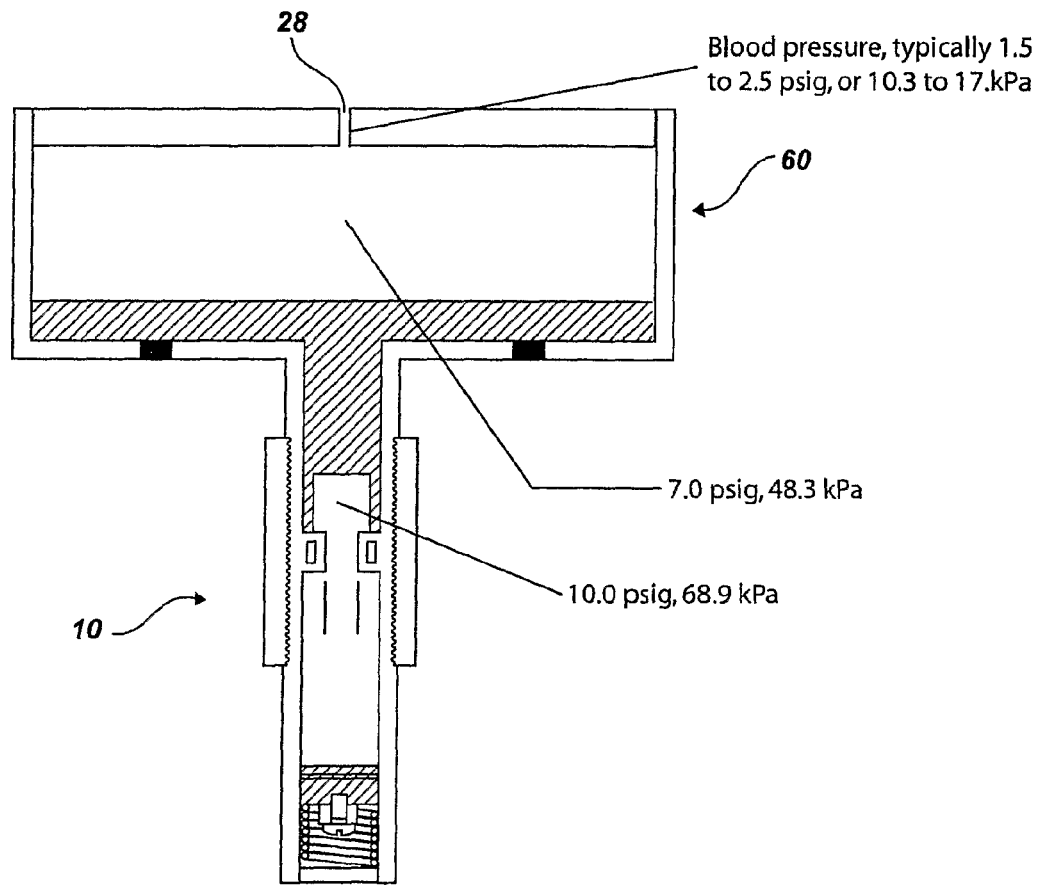
FIG. 7 is a cross-sectional view of FIG. 6 showing typical operating pressures in accordance with one embodiment of the present invention.

As seen in FIGS. 5 through 7, the delivery amplifier 60 can be operatively connected to the delivery piston or can be a single integral piece formed as part of the delivery piston. The delivery amplifier can have a first portion 62 proximal to the dispense fluid reservoir 26 and a second portion 64 distal to the dispense fluid reservoir, where the first portion has a larger cross-section than the second portion. In one embodiment, the delivery amplifier can include a first cylinder and an adjacent second cylinder having a diameter larger than the first. Further, the delivery amplifier can include vents 66 which prevent suction (or a vacuum region) from restraining the delivery piston.

The osmotic amplifier works by capitalizing the movement of the delivery piston as it is driven by osmotic pressure. By using this motion to drive a piston in a reservoir with a larger cross sectional area, more fluid can be forced out of the pump. The required dimensions of the membrane and reservoirs for a desired flow rate can be calculated by analysis of the geometry of the pump. Since the cross sectional area of the reservoirs is constant, the only change will be in the depth of the reservoirs. Knowing this, the desired flow rate can be divided by the cross sectional area of the delivery reservoir to find the rate of change in depth of the reservoirs. Multiplying this rate of change in depth by the cross sectional area of the solution reservoir 20 gives the desired flow rate into the solution reservoir, which is also the desired flow rate across the membrane 12. For a system based on water-NaCl, the resulting equation is of the form $$J = P * \frac{A_{NaCl}}{A_D}, \tag{1}$$

where J is the flow rate across the membrane, P is the desired rate of delivery, $A_{NaCl}$ is the cross sectional area of the solution reservoir, in this case, the NaCl reservoir, and $A_D$ is the cross sectional area of the dispense fluid reservoir. Although this equation is for a water-NaCl solution, it can be modified for any solution by simply using the cross-sectional area of the pertinent solution reservoir, thus giving $A_{KCl}$, or $A_{solute}$. Once the flow rate across the membrane is found, the required area of the semi-permeable membrane can be found using the equation given by $$J = KA\Delta\pi, \tag{2}$$

where K is the permeability of the membrane, A is the area of the membrane, and $\Delta\pi$ is the osmotic pressure difference across the membrane. This equation assumes negligible hydrostatic back pressure which may oppose the osmotic pressure difference.

The dispense pumps of the present invention can be designed for use under a wide variety of pressure and temperature conditions. Typically, in order for the pump to work, it should have the capability to overcome any back pressures resulting from the environment in which it is used. In medical applications, this back pressure would be the blood pressure of a patient, which is typically 1.5 to 2.5 psig (10.3 to 17.2 kPa). For example, the pressure in the drug reservoir can be about 5 psig (about 30 kPa) above blood pressure, and the pressure to drive the delivery piston can be about 3 psig (about 20 kPa) above that of the drug reservoir. These typical operating pressures are shown in the pump of FIG. 7. Advantageously, the dispense pumps of the present invention can operate under environments having pressures in excess of about 100 psig up to about 150 psig and in some cases up to about 300 psig. Preferably, the dispense pumps can be configured to operate at relatively high pressures from about 150 psig to about 250 psig. Similarly, the materials can be readily selected to withstand temperatures of greater than about 121° C., such as about 150° C. At higher temperatures the flow rate will tend to increase for most systems. Thus, those skilled in the art can take into account the expected delivery temperatures in order to adequately predict the delivery rate.

In summary, solvent can be osmotically driven through the membrane into the solution reservoir causing pressure to build sufficient to drive the delivery piston forcing fluid from the dispense fluid reservoir. A number of advantages can be realized using the devices of the present invention. In accordance with an embodiment of the present invention, a constant and accurate low flow rate pump can operate continuously for one year or more without maintenance while withstanding high back pressures and elevated temperatures. This extended operating time can be accomplished either using the osmotic amplifier device, or by utilizing increased sized reservoirs of solvent and solution.

The dispense pumps of the present invention can operate continuously without batteries or external power supplies. The dispense flow rate can be sustained for the duration of the dispensing period. Although the device can be configured otherwise, low flow rates on the order of microliters per hour can be readily achieved. Advantageously, the flow rates from the present invention can be substantially continuous within a very tight tolerance and substantially without pulsed flow. High pressures can be generated which are capable of overcoming back pressures typically encountered in a wide variety of conventional applications. Further, in some embodiments of the present invention, the osmotic dispense pump can be operable at elevated temperatures up to about 150° C. and frequently up to about 121° C. Materials used in the dispense pump can be carefully selected to have low chemical reactivity in the intended environment. Further, the pumps of the present invention can be highly portable due to the ability to manufacture such devices at small dimensions on the order of about 0.25 to about 10 inches length, and about 0.25 to about 5 inches width, although sizes outside this range can also be designed.

The dispense pumps of the present invention can be used to deliver a wide variety of fluids. Once the dispense pump is formed, a fluid can be dispensed by charging the device. The solvent reservoir can be charged with a solvent which is permeable to the semi-permeable membrane. Similarly, the solution reservoir can be charged with a solution of the solvent and a solute such that the solution has a concentration of solvent which is lower than a concentration of solvent in the solvent reservoir. Further, the dispense fluid reservoir can be charged with a fluid to be dispensed through the outlet.

Once the use of the dispense pump is no longer needed and/or once the dispense fluid is depleted, the pump may be reset and reused. This can be done by removing the contents of the reservoirs and appropriately re-filling them as desired. Additionally, the pistons will need to be reset, and the spring, if such configuration is used, would need to be reset to a compressed position.

In another alternative aspect, the dispense fluid can be two or more different and distinct materials. In one embodiment, the dispense fluid reservoir can contain two smaller reservoirs. In this instance, the reservoirs are preferably aligned so that one smaller reservoir will be completely depleted before the second smaller reservoir. The reservoirs can be separated by a barrier configured to separate the dispense fluids when housed near each other, and also to allow dispensing of the second fluid from the outlet after depletion of the first fluid. This configuration can include a means of puncturing the barrier which is attached to the outlet wall, or a perforated hole subject to pressure forces aligned with the outlet. Optionally, the second fluid can be immiscible in the first fluid and can be contained within a common reservoir.

Alternatively, or in addition, multiple reservoirs can allow for simultaneous delivery of multiple fluids. In this case, a barrier or separation wall within the delivery reservoir can be preferably used which is in-line with the axis of the flow channel. Alternatively, for the delivery of multiple fluids, the osmotic force can be directed to more than one delivery piston associated with individual dispense fluid reservoirs.

Commercial applications for the dispense pumps of the present invention are not particularly limited. However, a number of applications are currently envisioned as particularly suitable for these dispense pumps. For example, the dispense pumps can be useful for flowing reference junctions in pH sensors, ORP sensors or the like, internal or external drug delivery (with human and veterinary applications), localized lubrication system for machinery, cooling devices in microelectronics and MEMS, fragrance delivery systems, and any application requiring continuous delivery of small volumes of fluid for extended periods of time.

One practical application of the present osmotic pump device is for use as an electrolyte delivery system in potentiometric sensors. The osmotic pump provides the driving force for electrolyte flow in the reference half cell of these sensors. Potentiometric sensors, such as pH, redox and ion selective electrodes, are galvanic electrochemical cells consisting of two half cells, a measuring half cell and a reference half cell, each with an electrode and electrolyte solution. The measuring half cell generates an electrical potential in proportion to the property being measured, such as the pH of water and aqueous solutions. The reference half cell consists of three functional components: (i) a reference electrode frequently made of silver and silver chloride, (ii) a reference electrolyte usually a potassium chloride salt solution in contact with the reference electrode, and (iii) a small porous plug, or junction, through which the electrolyte salt solution makes electrical contact sequentially with the solution being analyzed and the measuring half cell. Ideally, the reference half cell remains constant with known and unchanging potential, so that the measured potential between the two half cells is due only to the property of interest, for example pH.

On-line process applications, unlike laboratory applications, require the reference half cell to function in widely varying and extreme conditions of temperature, pressure, un-dissolved solids, strong chemical concentrations; and to do so continuously. These conditions threaten the stability of the reference half cell by creating unwanted changes in potential due to clogging and poisoning of the porous junction and by poisoning the reference electrolyte salt solution. An unstable reference electrode creates errors in the measurement.

A reference half cell with an external pressure source and electrolyte reservoir supplies a continuous low flow of clean electrolyte solution through the reference junction, thus preventing the plugging and poisoning of the junction and preventing the ingress of process chemicals into the half cell. A reference half cell with flowing electrolyte is considered to be the fastest and most accurate design but because of cumbersome, labor-intensive, installation and maintenance, it has not been well received by operators.

The osmotic devices described herein addresses the above requirements for a flowing reference half cell while solving the practical problems that burden external pressurization schemes. A low flow can be supplied of about 1 µL/hr for a period of 1 year with the capability of operating at different pressures and different temperatures. Process pH sensors are frequently cylindrical in shape, with diameters of about 25 mm and lengths ranging from about 125 mm to 250 mm. The osmotic pump shown in FIG. 1 fits well into these size constraints. Since the osmotic device is completely self-sustaining and self-contained, with a pressurized electrolyte supply, it can be built directly into the process pH sensor or onto another potentiometric type sensor.

Another practical application of the present osmotic pump device is for use in drug delivery. Actuation of the micro-dispense pump is accomplished as water, driven by a chemical potential, crosses the osmotic membrane and enters a salt chamber, as described earlier. This increase in volume in the salt chamber forces the expansion membrane to deflect into the drug reservoir. As the expansion membrane pushes into the reservoir, the drug is dispensed via an outlet port. Example specifications for a suitable device in accordance with the present invention include the ability to: (i) deliver a generic liquid at a rate of one microliter per hour, (ii) deliver the liquid in a continuous manner (i.e. no pulse flow), (iii) sustain target delivery rate for a period of one week, (iv) provide operation without external power source, (v) develop pressures capable of overcoming large back pressures, (vi) maintain volumetric accuracy ±5%, and (vii) drug volume to total volume ratio of 1:3. To meet these specifications, the osmotically driven micro-dispense pump shown in FIG. 1 can be employed. For this arrangement, the pump is composed of the following layers: a flow limiter, an osmotic membrane, a salt chamber, an impervious expansion membrane, a drug reservoir/device interface.

The flow rate of the osmotic pump is proportional to the exposed surface area of the osmotic membrane. The water-side flow limiter layer restricts the exposure of the osmotic membrane to the water, and thereby regulates the flow. Made of acrylic, the limiter can have a thickness of 1 mm. Differing from layer shown in FIG. 1, an alternative design of the limiter has an inner diameter of 0.635 mm.

The osmotic membrane separates the osmotic agent (sodium chloride) from the solvent (water), and regulates the flow of solvent across the chemical gradient. A cellulose acetate membrane is currently used, and is available from GE Osmonics, among others.

The osmotic agent is housed in the salt chamber. The volume of the chamber is equal to the volume of salt necessary to maintain a supersaturated aqueous sodium chloride solution for the duration of the dispensing period. Made of acrylic, the chamber is 1 mm thick and has an inner diameter of 8 mm. Differing from the layer shown in FIG. 1, a salt-side flow limiter has been incorporated into the design of the salt chamber. Like the water-side limiter, the salt-side flow limiter restricts the exposure of the osmotic membrane to the osmotic agent, thereby regulating the flow. Made of acrylic, the flow limiter has a thickness of 0.5 mm and an inner diameter of 0.635 mm which is the same as the water-side flow limiter.

The expansion membrane seals the salt chamber and allows for actuation of the pump. As osmosis draws water into the salt chamber, the impervious expansion membrane plastically deforms to compensate for the increased volume. This deformation pushes into the drug reservoir, thereby expelling its contents. The expansion membrane can be made of a thin film of polyvinylidene chloride (PVDC).

The liquid to be delivered by the pump is stored in the drug reservoir. The reservoir has a spherical geometry that receives the natural shape of the expanded expansion membrane, and has maximum diameter of 10 mm. The reservoir has an outlet port that connects directly to a threaded counter bore, enabling the device to interface with tubing.

A pump was designed according to FIG. 6, including a delivery amplifier 60 having a solution reservoir 20, a delivery piston 68, and a dispense fluid reservoir 26. The wall with the outlet was 8 cm in diameter, the body of the pump, excluding the delivery amplifier section, was 1 cm in diameter, and the length of the pump was 10 cm. Using the equations presented earlier, with the pump designed to pump 100 ml of fluid at a rate of 1 ml per hour. Multiplying this rate by the ratio of cross-sectional areas of the reservoirs, shows that the desired delivery rate to be 64 times greater than the osmotic flow rate. When compared to a pump without an osmotic amplifier, the delivery rate of the pump including the osmotic amplifier can be increased up to about 1000 times.

EXAMPLES

The following are examples which illustrate various osmotic dispense pumps, methods of forming the pumps and methods of dispensing fluid using the pumps in accordance with the present invention. However, it is to be understood that the following are only exemplary or illustrative of the application of the principles of the present invention. Numerous modifications and alternative compositions, methods, and systems can be devised by those skilled in the art without departing from the spirit and scope of the present invention. The appended claims are intended to cover such modifications and arrangements. Thus, while the present invention has been described above with particularity, the following Examples provide further detail in connection with several specific embodiments of the invention.

Device Design and Testing Conditions

Among the following examples, two different semi-permeable materials are utilized, polyimide and porous glass. The devices using polyimide as the semi-permeable membrane are capable of operation at temperatures up to and including 75° C., and at pressures up to 1.03 MPa. The devices using porous glass operate at temperatures in excess of 121° C., unless pressures above 172.4 kPa are applied, in which case, operation is limited to temperatures less than 50° C.

One semi-permeable membrane material employed is polyimide, because porosity and filtration are similar to cellulose acetate, and because of its capability to operate at higher temperatures than cellulose acetate. Porous glass or micro-porous Vycor 7930 glass are also used in the present study. The three examples below include: (i) a device using a semi-permeable membrane of polyimide, (ii) a device using a semi-permeable membrane of polyimide with a polymer mesh for added rigidity and support as different operation pressures are applied, and (iii) a device using a membrane consisting of Vycor 7930 porous glass. The devices are designed to deliver fluid at a continuous rate of approximately 1 micro-liter/hr for a duration of 1 year at different pressure and temperature operating conditions.

A schematic diagram of the exemplary device is shown in FIG. 1. The feature which controls the overall flow rate resulting from osmosis is the size of the inlet orifice which leads to the salt chamber. The orifice area, A, allows contact between the water and salt reservoirs, which restricts the amount of transport of water across the membrane. This restriction controls the amount of expansion in the osmotic agent reservoir, which, in turn, controls the amount of fluid pumped out of the delivery fluid reservoir. The volumetric flow rate across the osmotic membrane J is given by $$J = KA(\sigma \Delta \pi - \Delta P) \quad (3)$$

where $\Delta \pi$ is the difference in osmotic pressure across the membrane, and $\Delta P$ is the total internal hydrostatic pressure required to force flow through the outlet of the pumping device. The osmotic pressure $\pi$ is given by $$\pi = SiRT \quad (4)$$

For the present device, the difference in osmotic pressure is 35.6 MPa (or 5156 psig) when pure water is in contact with saturated sodium chloride solution. The time duration of operation, D, is given as $D=(V/Q)(0.95)$. Using this relation, the pump reservoir volume to achieve a flow rate of 1 micro-liter/hr for one year is 9221 micro-liters.

In order to obtain constant flow rates, three factors should be considered. First, the osmotic agent can maintain a saturated state during operation. Second, environmental osmotic activity should remain constant or be negligible. Third, the reflection coefficient should remain constant or close to unity. The theoretical amount of osmotic agent required is then determined using the equation given by $$M_s = V_d \cdot S/(1-(S/\rho_s)) \quad (5)$$

Here, note that $V_d$ is the initial volume of the osmotic agent reservoir. From this equation, the amount of sodium chloride required for continuous operation for one year is 3.97 g.

If all of the variables within Eqn. (3) are held constant, then increasing the area A gives an increased flow rate. As the water passes into the osmotic agent reservoir, pressure increases behind the piston forcing the delivery fluid out of the delivery fluid reservoir.

To insure proper alignment of the flow orifices and flow passages to and from the osmotic membrane, and to reduce leakage potential, a unique membrane housing was employed, which is designed as described above. A schematic drawing of this housing is shown in FIG. 2. This arrangement was incorporated on all three of the devices considered. The portion of the osmotic membrane which was not used to regulate the flow was then completely enclosed within an elastomer gasket made of RTV 630, as shown in FIGS. 1 and 2.

Each osmotic pump was connected to a 0.76 mm internal diameter clear tube which vertically ascends a 204 cm long scaled grid. The dispense fluid was colored for increased visibility with respect to this grid. Because testing extended over a period of days, the fluid level was recorded using video imaging from which the volume displaced by the pump was calculated. At the top of each tube was a small pressure vessel along with a gauge and a pressure connection. When specific back pressure is required, pressure is applied to this connection. All gauges had an accuracy of ±7 kPa. All pressures were maintained within ±34 kPa. When the osmotic devices were tested at elevated temperature, the osmotic pumping apparatus was placed within a Tenney Jr. Corp. Thermal Chamber. With this arrangement, all temperatures were generally maintained within ±1° C.

In the second of the three devices tested, a supportive mesh was installed behind the polyimide membrane on the solvent side for reinforcement. This PTFE material P/N ET 8120 mesh was acquired from Internet Inc. The mesh was molded into the RTV seal during production to avoid mesh slippage during assembly, and to keep the mesh as rigid as possible during operation as different levels of pressure and temperature were encountered.

In the third osmotic dispense pump tested, Corning Vycor 7930 porous glass was used as the semi-permeable membrane. The material was employed because the average pore size is about 40 angstroms in diameter, and because material specifications indicate the ability to maintain this porosity at elevated temperatures. Each 6.35 mm diameter disk was about 1 mm thick, and was mounted using an arrangement similar to the one shown in FIG. 2, with face seals made of RTV 630 silicone added on both the upper and lower surfaces. The lower seal controls the amount of area exposed to the osmotic agent. The main purpose of the upper seal was to hold the porous glass membrane in place. This was accomplished as the upper seal conforms to the porous glass disk dimensions as its retainer was tightened.

Test Results

Figure 8:
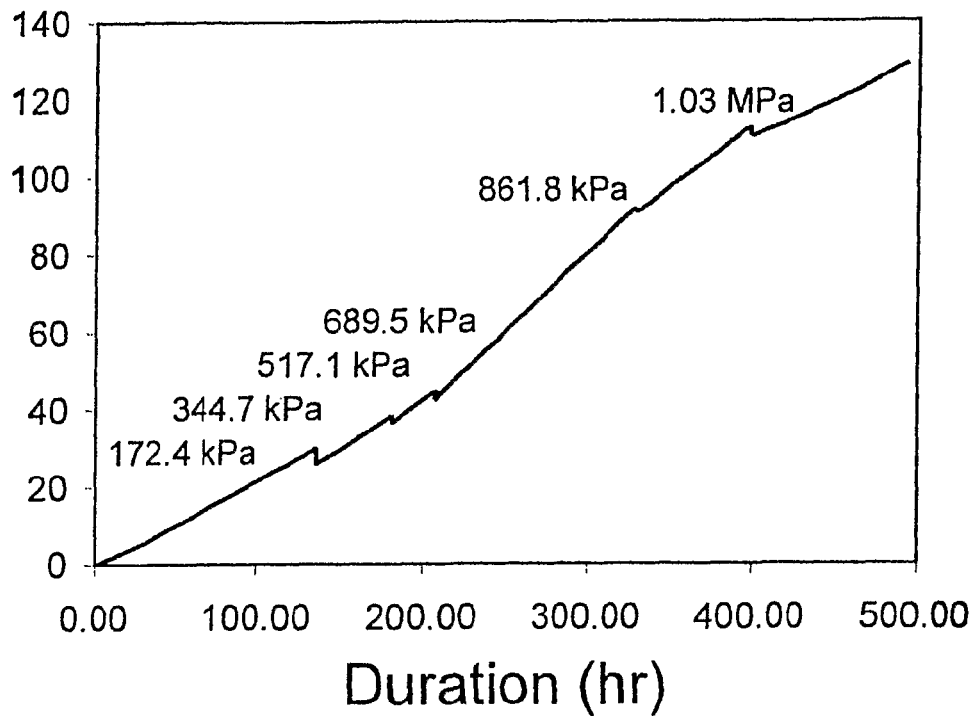
FIG. 8 is a graph of displacement of a vertical column of water with time produced by the osmotic pump with a polyimide membrane for ambient temperature and gauge pressures from 0 to 1.03 MPa in accordance with one embodiment of the present invention.

The osmotic pump devices with polyimide semi-permeable membranes were tested at different pressures and temperatures. The orifice size employed was 1.32 mm in diameter. FIG. 8 and Table 1 give flow rate information in the form of VWCH as dependent upon time duration, for different back pressures. Table 1 shows volumetric flow rate data produced by the osmotic pump with a polyimide membrane for ambient temperature and gauge pressures from 0 to 1034.2 kPa.

TABLE 1

| Pressure (kPa) | Flow Rate (microL/hr) |
|---|---|
| 0 | 1.02 |
| 344.7 | 0.94 |
| 517.1 | 1.01 |
| 689.5 | 1.8 |
| 861.8 | 1.46 |
| 1034.2 | 1.5 |

Figure 9:
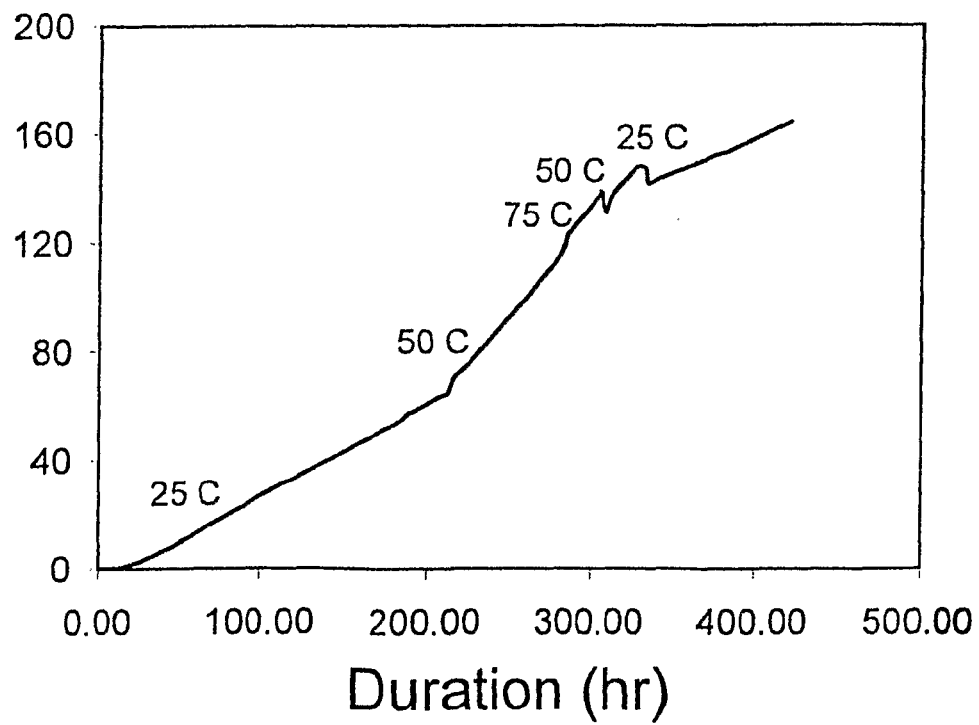
FIG. 9 is a graph of displacement of a vertical column of water with time produced by the osmotic pump with a polyimide membrane for temperatures from 25° C. to 75° C., and a gauge pressure of 172.4 kPa in accordance with one embodiment of the present invention.

The increased flow rates at higher back pressures are due to stretching and distortion of the semi-permeable membranes employed within the flow orifice locations. As this occurs, larger membrane surface areas are exposed to the osmotic agent. FIG. 9 and Table 2 present VWCH data as dependent upon D for temperatures up to 75° C. Table 2 shows volumetric flow rate data produced by the osmotic pump with a polyimide membrane for temperatures from 25° C. to 75° C., and a gauge pressure of 172.4 kPa.

TABLE 2

| Flow Rate uL/hr | Temperature (° C.) | Pressure (kPa) |
|---|---|---|
| 1.4 | 25 | 172.4 |
| 3.17 | 50 | 172.4 |
| 3.48 | 75 | 172.4 |
| 3.18 | 50 | 172.4 |
| 1.2 | 25 | 172.4 |

At temperatures above 75° C., flow rates either decrease significantly or stop altogether. This is because of permanent degradation of the polyimide membranes at such elevated temperature levels. At ambient pressure and temperature, the flow rate was approximately 1.02 µL/hr.

Figure 10:
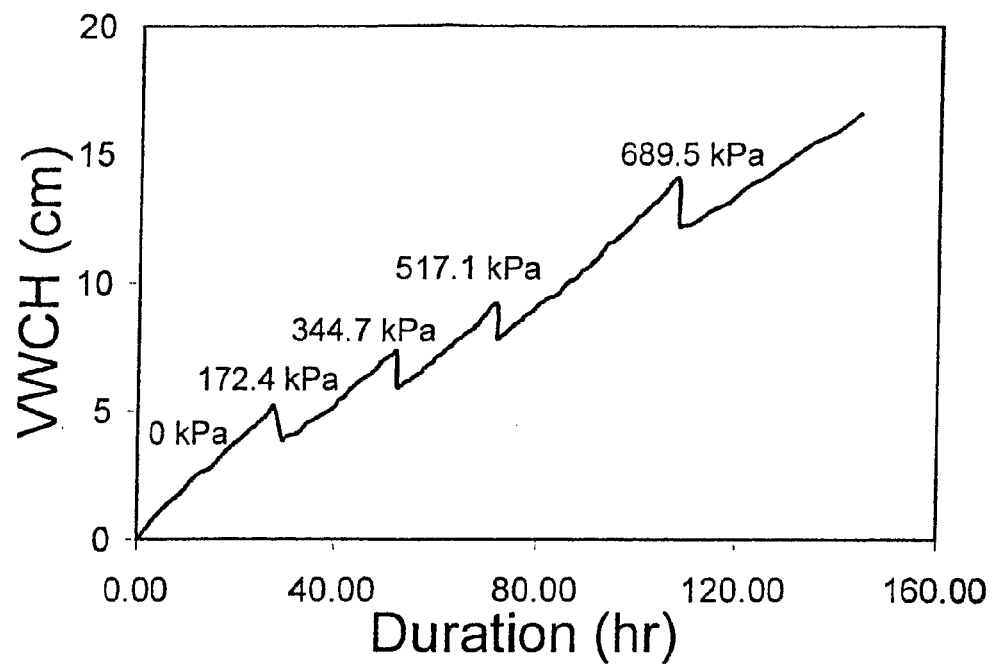
FIG. 10 is a graph of displacement of a vertical column of water with time produced by the osmotic pump with a polyimide membrane with mesh support for ambient temperature and gauge pressures from 0 to 689.5 kPa in accordance with one embodiment of the present invention.

Because of membrane stretching and distortion at elevated pressure levels, PTFE material P/N ET 8120 mesh material was used to mount and support the polyimide osmotic membranes, although other mesh or porous support materials could be used. With this arrangement, the orifice diameter size was again 1.32 mm. VWCH results obtained with this configuration are shown in FIG. 10 and Table 3. Table 3 shows volumetric flow rate data produced by the osmotic pump with a polyimide membrane with mesh support for ambient temperature and gauge pressures from 0 to 689.5 kPa.

TABLE 3

| Pressure (kPa) | Flow Rate (uL/hr) |
|---|---|
| 0 | 0.8 |
| 172.4 | 0.74 |
| 344.7 | 0.8 |
| 517.1 | 0.78 |
| 689.5 | 0.7 |

Compared with the results obtained with no mesh support, a flow rate decrease of approximately 20 percent was observed at least partially because the mesh covers portions of the exposed surface areas of the osmotic membranes. Overall, smaller variations of flow rates were observed as back pressure was varied when the mesh was employed because of its ability to minimize membrane distortion as pressure increases.

Figure 11:
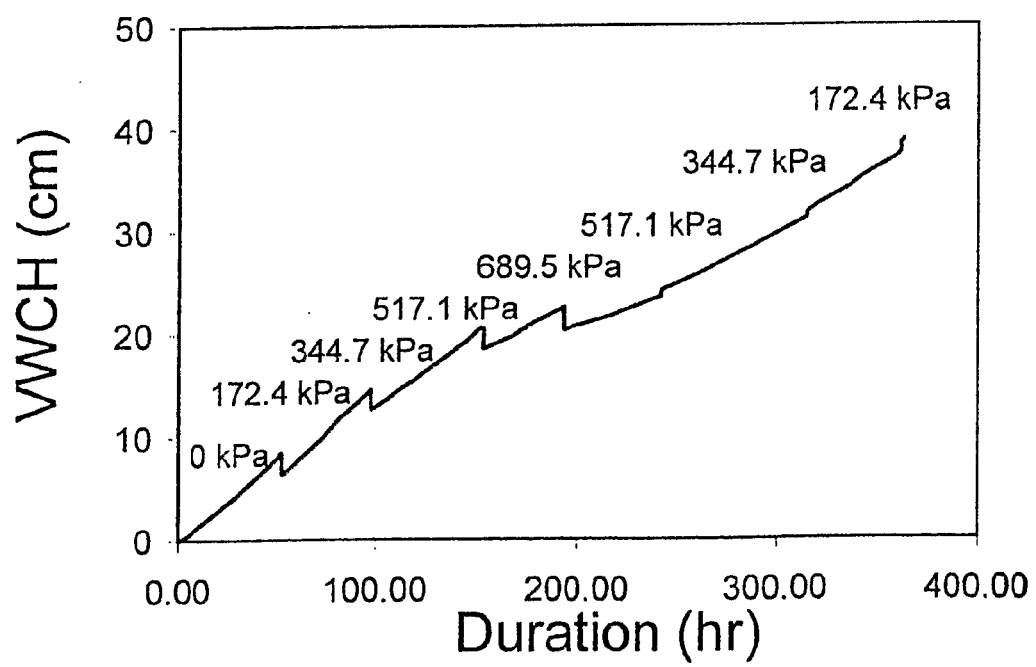
FIG. 11 is a graph of displacement of a vertical column of water with time produced by the osmotic pump with a porous glass membrane for ambient temperature and gauge pressures from 0 to 689.5 kPa in accordance with one embodiment of the present invention.

Test results obtained with the porous glass osmotic membranes are presented in FIG. 11 and Table 4. Table 4 shows volumetric flow rate data produced by the osmotic pump with a porous glass membrane for ambient temperature and gauge pressures from 0 to 689.5 kPa

TABLE 4

| Pressure (kPa) | Flow Rate (uL/hr) |
|---|---|
| 0 | 0.7 |
| 172.4 | 0.8 |
| 344.7 | 0.65 |
| 517.1 | 0.5 |
| 689.5 | 0.33 |
| 517.1 | 0.45 |
| 344.7 | 0.59 |
| 172.4 | 0.63 |
| 0 | 0.67 |

At the start of this test, when the temperature and pressure were at ambient conditions, the volumetric flow rate was 0.7 micro-liter per hour. Afterwards, VWCH values were measured as the applied osmotic pressure Pb incrementally from 0 to 689.5 kPa, and then, as the pressure decreases incrementally from 689.5 to 0 kPa at ambient temperature. With this arrangement, the flow rate reduces by 10 to 20 percent as the pressure is increased by each 172.4 kPa increment. When ambient pressure was applied, the porous glass devices operated successfully at temperatures greater than 121° C. However, when applied osmotic gauge pressure exceeded 172.4 kPa, operation was limited to temperatures less than 50° C.

Figure 12:
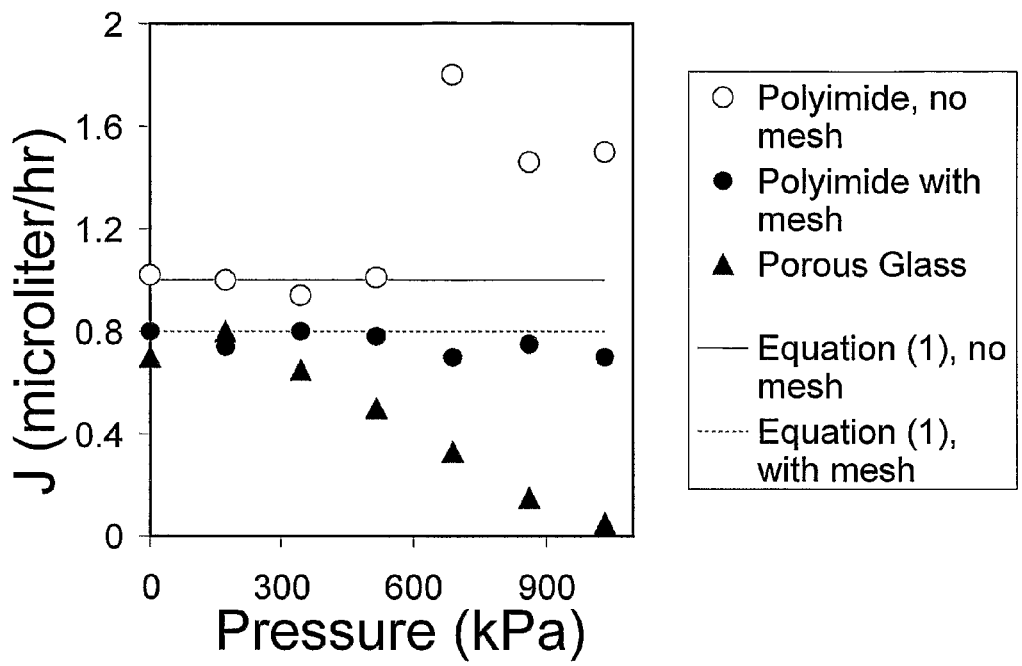
FIG. 12 is a graph of variation of volumetric flow rate at ambient temperature with applied back gauge pressure for osmotic pumping devices with different permeable membranes in accordance with one embodiment of the present invention.

Osmotic device volumetric flow rate variations with Pb are further illustrated by the results given in FIG. 12. Here, the volumetric flow rate J is presented as it varies with Pb for all three examples of osmotic devices. Here, much larger variations of J with Pb for the porous glass device are apparent compared with the nearly constant flow rates with applied osmotic back pressure for the polyimide with mesh device. Also included in FIG. 12 are theoretical flow rates for the two types of polyimide devices for no mesh support and with mesh support. From equation (3), the difference between the osmotic pressure and internal hydrostatic pressure, or the pressure difference required to overcome friction to generate piston displacement is about 68.9 kPa. The orifice area A and permeability K (determined experimentally) are $1.37 \times 10^{-6}$ m$^2$ and $3.05 \times 10^{-12}$ m$^3$/Ns, respectively. The theoretical flow rate for the no mesh condition is then $2.78 \times 10^{-13}$ m$^3$/s, or approximately 1 µL/hr. When the mesh is employed, the area, A, is reduced by 20 percent, which results in a flow rate of about 0.8 µL/hr. FIG. 12 shows that this latter value compares well with data measured using a device with a polyimide membrane and mesh support.

Figure 13:
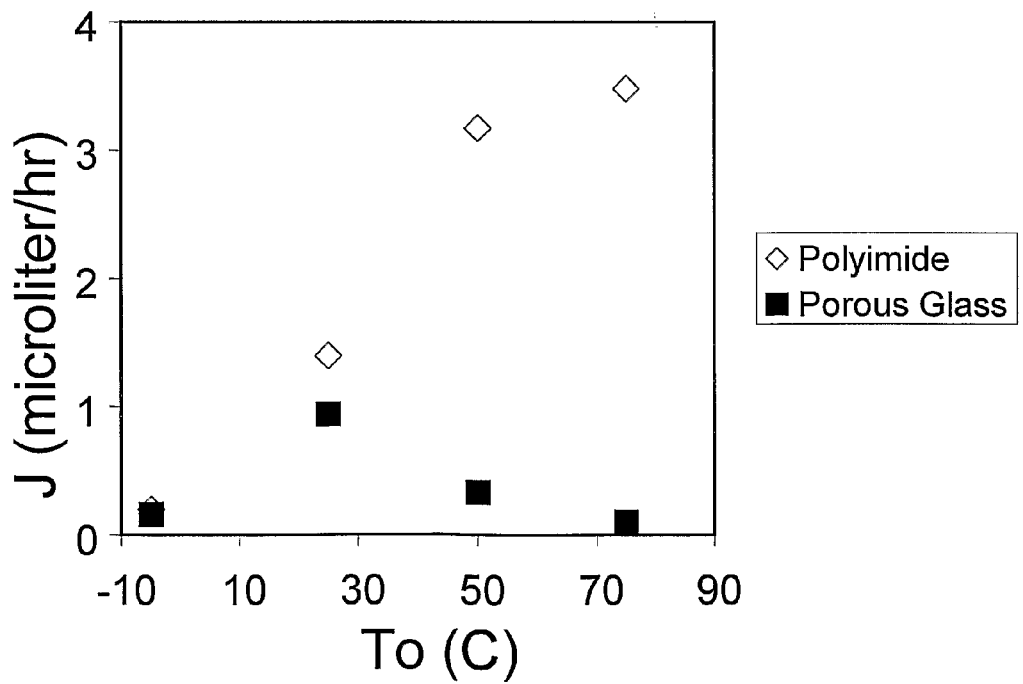
FIG. 13 is a graph of variation of volumetric flow rate at 172.4 kPa back pressure with applied temperature of the osmotic pumping devices with different permeable membranes in accordance with one embodiment of the present invention.

The variation of volumetric flow rate with applied osmotic temperature is shown in FIG. 13 for the polyimide and porous glass devices. These data were obtained at a constant osmotic back pressure of 172.4 kPa gauge. In general, the porous glass devices show decreased volumetric flow rate with increased osmotic temperature. In contrast, volumetric flow rate consistently increases with increased osmotic operation temperature for the polyimide membrane devices, which is consistent with Eqns. (3) and (4).

Of the osmotic pumping devices tested, the one which produces stable flow rates over the widest ranges of temperature and pressure, employs a polyimide membrane with a PTFE backing support mesh. The device operated in a satisfactory fashion at temperatures from −5 to 75° C. and at gauge back pressures up to 1.03 MPa, with predicted flow rates in agreement with theoretical predictions. Without the backing support mesh, the polyimide membrane is believed to stretch and distort as back pressures increase, which results in some fluctuation in flow rates, since flow rates increase substantially at higher back pressures. When ambient pressure is applied, the porous glass devices operate successfully at temperatures greater than 121° C. As applied osmotic gauge pressure exceeds 172.4 kPa, operation was limited to temperatures less than 50° C.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A high pressure osmotic dispense pump, comprising:
    a) a semi-permeable membrane which is substantially free of distortions and lateral stretching stresses, said semi-permeable membrane oriented within a delivery chamber body, and being secured against longitudinal movement with respect to the delivery chamber body by lateral clamping between at least two housing members, said lateral clamping having only lateral forces with respect to a plane of the semi-permeable membrane so as to maintain the semi-permeable membrane substantially free of distortions and lateral stretching stresses, said housing members being secured against longitudinal movement with respect to the delivery chamber body;
    b) a solvent reservoir oriented within the delivery chamber body, and in fluid communication with the semi-permeable membrane and including a solvent piston which is movable in response to a change in a fluid volume within the solvent reservoir;
    c) a solution reservoir oriented within the delivery chamber body, and in fluid communication with the semi-permeable membrane and including a delivery piston which is movable in response to a change in a fluid volume within the solution reservoir;
    d) a fluid reservoir oriented within the delivery chamber body, and adjacent the delivery piston opposite the solution reservoir and being fluidly isolated from each of the solvent reservoir and solution reservoir and having an outlet for dispensing a fluid contained in the fluid reservoir;
    e) a flow channel between the solvent reservoir and the solution reservoir formed by the at least two housing members, wherein the cross sectional area of the semi-permeable membrane in the flow channel is substantially smaller than the cross sectional area of the solvent reservoir and the solution reservoir, wherein a diameter of the flow channel is less than half a diameter of the solvent reservoir and the solution reservoir; and
    f) a spring oriented within the delivery chamber body, and operatively oriented adjacent the solvent piston opposite the solvent reservoir and configured to displace the solvent piston towards the semi-permeable membrane.

2. The pump of claim 1, wherein each of the solvent reservoir, solution reservoir, and fluid reservoir have rigid walls.

3. The pump of claim 1, wherein interior surfaces of at least one of the solvent reservoir, solution reservoir, and fluid reservoir include a coating of polytetrafluoroethylene.

4. The pump of claim 1, wherein the pump is configured to deliver the fluid at a flow rate which is substantially continuous.

5. The pump of claim 1, wherein the membrane is formed of a material selected from the group consisting of polyamide, porous glass, and cellulose acetate.

6. The pump of claim 1, wherein the solvent piston and the delivery piston are formed of a material selected from the group consisting of polyether ether ketone, polyimide, polycarbonate, glass reinforced polytetrafluoroethylene, and composites or combinations thereof.

7. The pump of claim 1, wherein the semi-permeable membrane has an exposed surface area and a covered surface area each oriented on a common side of the semi-permeable membrane, said exposed surface area being smaller than the covered surface area.

8. The pump of claim 1, further comprising a support mesh oriented within the delivery chamber body, and oriented adjacent the semi-permeable membrane.

9. The pump of claim 1, further comprising a modulator plate oriented within the delivery chamber body, and oriented between the semi-permeable membrane and the solvent reservoir, said modulator plate having a plurality of holes corresponding to a plurality of delivery flow rates.

10. The pump of claim 1, further comprising a flow activation valve oriented within the delivery chamber body, and operatively connected between the solvent reservoir and the solution reservoir such that flow of a solvent across the semi-permeable membrane can be selectively controlled.

11. The pump of claim 10, wherein the flow activation valve includes a cylindrical member having an open bore laterally therein such that a central axis of the open bore is substantially perpendicular to a central axis of the cylindrical member.

12. The pump of claim 11, wherein the flow activation valve is oriented between the semi-permeable membrane and the solvent reservoir.

13. The pump of claim 1, further comprising a delivery amplifier oriented within the delivery chamber body, and operatively connected to the delivery piston, said delivery amplifier having a first portion proximal to the fluid reservoir and a second portion distal to the fluid reservoir, said first portion having a larger cross-section than the second portion.

14. A method of forming a high pressure osmotic dispense pump as in claim 1, comprising:
    a) forming a flow channel in the at least two housing members wherein the flow channel in each housing member is substantially aligned and forms a fluid connection between a solvent reservoir and a solution reservoir; and b) securing a semi-permeable membrane between the at least two housing members using substantially only securing forces which are perpendicular to the semi-permeable membrane.

15. The method of claim 14, wherein the step of securing is performed by orienting the semi-permeable membrane between the at least two housing members and inserting at least two alignment members into corresponding alignment channels which are substantially perpendicular to the semi-permeable membrane such that the at least two housing members are pressed towards one another with substantially only forces acting perpendicular to the semi-permeable membrane.

16. The method of claim 14, further comprising the step of coating an interior surface of at least one of the solvent reservoir, solution reservoir, and delivery reservoirs with a low friction material.

17. A method of dispensing a fluid using the pump of claim 1, comprising:
a) charging the solvent reservoir with a solvent which is permeable to the semi-permeable membrane;
b) charging the solution reservoir with a solution of the solvent and a solute, said solution having a concentration of solvent which is lower than a concentration of solvent in the solvent reservoir; and
c) charging the fluid reservoir with a fluid to be dispensed through the outlet.

18. The method of claim 17, wherein the pump is capable of operating at high pressures from about 100 psig to about 300 psig.

19. The method of claim 17, wherein the solvent is water and the solution is aqueous sodium chloride.

20. The method of claim 17, wherein the pump is capable of operating at a temperature up to about 150° C.

21. The pump of claim 1, further comprising a gasket oriented between the at least two housing members and used to retain edges of the semi-permeable membrane, and maintain the membrane substantially free of distortions and lateral stretching stresses.

22. The pump of claim 1, wherein the at least two housing members are discrete from, and secured from longitudinal movement within, the delivery chamber body surrounding the at least two housing members.

* * * * *